US00PP22052P2

(12) United States Plant Patent
Van Spronsen et al.

(10) Patent No.: US PP22,052 P2
(45) Date of Patent: Aug. 2, 2011

(54) ***CHRYSANTHEMUM* PLANT NAMED 'POWER ROSÉ'**

(50) Latin Name: *Chrysanthemum×morifolium*
Varietal Denomination: Power Rosé

(75) Inventors: Simon Van Spronsen, Niagara on the Lake (CA); Steven Van Spronsen, Niagara on the Lake (CA)

(73) Assignee: Willy's Greenhouse Ltd., Niagra on the Lake, ON (CA)

( * ) Notice: Subject to any disclaimer, the term of this patent is extended or adjusted under 35 U.S.C. 154(b) by 0 days.

(21) Appl. No.: 12/800,963

(22) Filed: Sep. 28, 2010

(51) Int. Cl.
*A01H 5/00* (2006.01)

(52) U.S. Cl. ..... Plt./297

(58) Field of Classification Search ..... Plt./297, Plt./286

See application file for complete search history.

*Primary Examiner* — Kent L Bell
(74) *Attorney, Agent, or Firm* — Penny J. Aguirre

(57) ABSTRACT

A new cultivar of daisy-type spray pot *Chrysanthemum,* 'Power Rosé', characterized by it's early, uniform and free flowering habit, its inflorescences with ray florets that are light burgundy in color with bright yellow disk florets that open from buds that are burgundy in color, its vigorous freely branched growth habit, its small leaved dark green foliage and its uniform, rounded and outward spreading plant habit.

2 Drawing Sheets

Botanical classification: *Chrysanthemum×morifolium.*
Variety denomination: 'Power Rosé'.

BACKGROUND OF THE INVENTION

The present invention relates to a new and distinct cultivar of *chrysanthemum* plant, botanically known as *Chrysanthemum×morifolium* 'Power Rosé' (syn. *Dendranthemum×grandiflora*) and hereinafter by its cultivar name, 'Power Rosé'.

The new *Chrysanthemum,* 'Power Rosé', was discovered by the Inventors as a naturally occurring branch mutation of *Chrysanthemum* cultivar 'Power Purple' (U.S. Plant Pat. No. 19,797) in a container in a greenhouse in September 2009 in Niagara on the Lake, Ontario, Canada.

Asexual reproduction of the new cultivar was first accomplished by one of the Inventors via stem cuttings in November 2009 in Niagara on the Lake, Ontario, Canada. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish by 'Power Rosé' as unique from all other cultivars of *Chrysanthemum* known to the Inventors.

1. The inflorescences of 'Power Rosé' have ray florets that are light burgundy in color with bright yellow disk florets that open from buds that are burgundy in color.
2. 'Power Rosé' is early flowering with daisy-type inflorescences about 3.8 cm in diameter when grown as a spray pot.
3. 'Power Rosé' exhibits a freely branched, uniform, rounded and outward plant habit.
4. 'Power Rosé' exhibits a uniform flowering response.
5. 'Power Rosé' exhibits small leaved dark green foliage.
6. 'Power Rosé' exhibits a vigorous growth habit.

In comparison to the parent plant, 'Power Purple', 'Power Rosé' has ray florets that are lighter and more red in color than the ray florets of 'Power Purple', which are deep purple in color. Based on its growth habit, flowering response and flower type, 'Power Rosé' can be most closely compared to 'Soft Cherie' (U.S. Plant Pat. No. 8,802), which differs from 'Power Rosé' in having light purple colored ray florets and 'Power Yellow' (U.S. Plant Pat. No. 18,175), which differs from 'Power Rosé' in having yellow ray florets.

BRIEF DESCRIPTION OF THE DRAWINGS

The accompanying colored photographs illustrate the overall appearance and distinct characteristics of the new *chrysanthemum,* 'Power Rosé'. The photographs were taken of plants grown in a 5-inch pan pot planted with 3 rooted cuttings and grown under greenhouse conditions for 10 weeks in Niagara on the Lake, Ontario, Canada.

Figure 1:
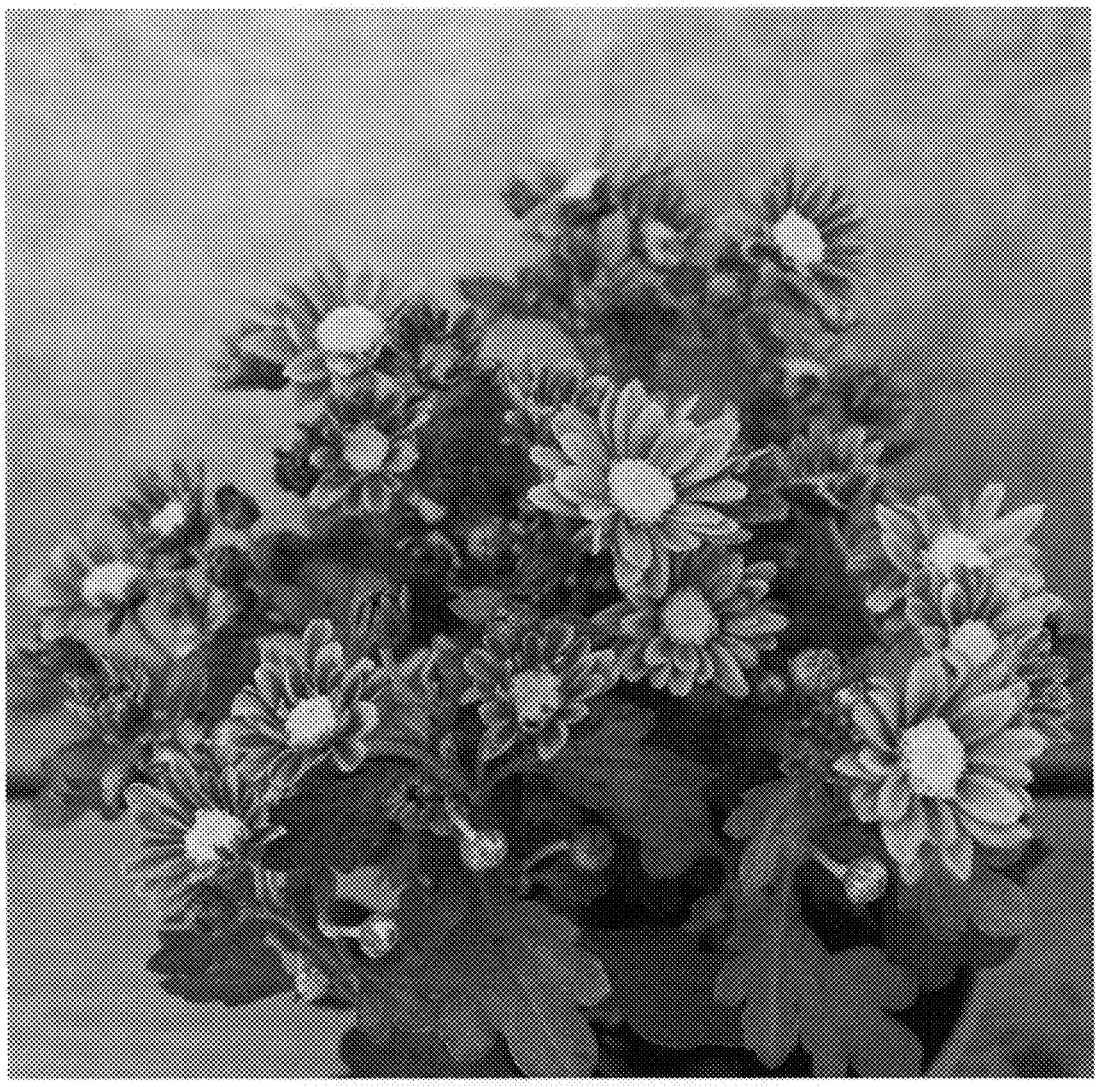
FIG. 1 is a photograph that provides a side view of a typical plant of 'Power Rosé' in bloom when grown as a spray-type.
Figure 2:
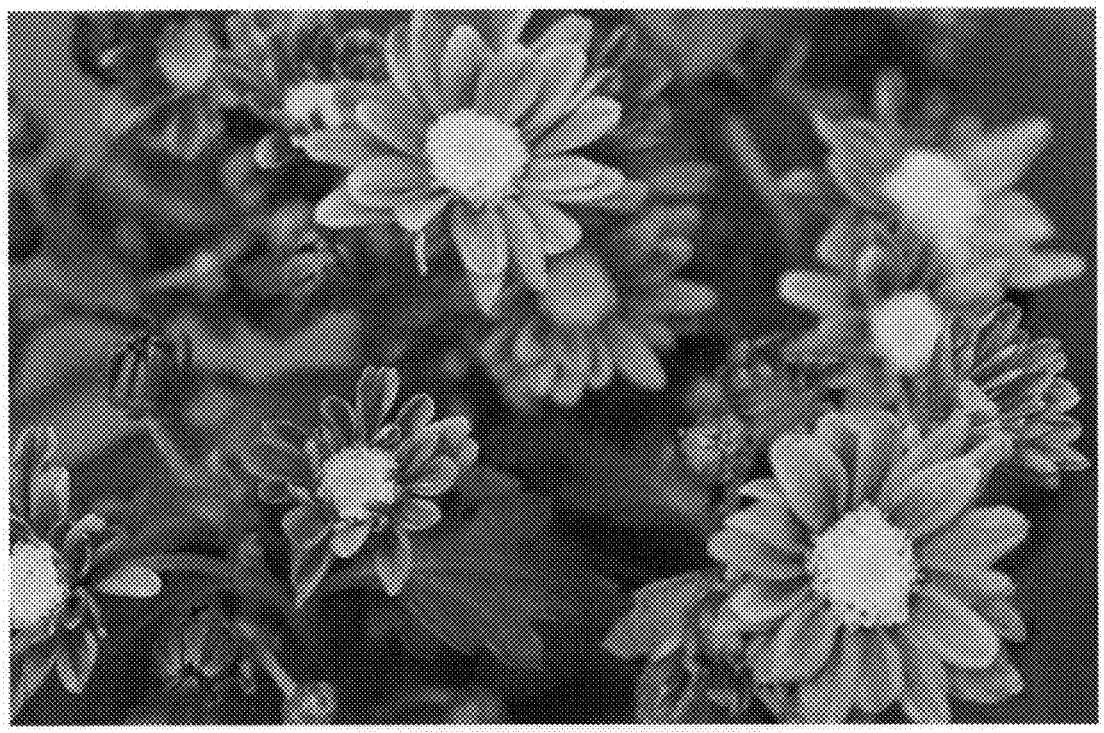

The photograph in FIG. 2 provides a close up view of the inflorescences of 'Power Rosé'.

Figure 3:
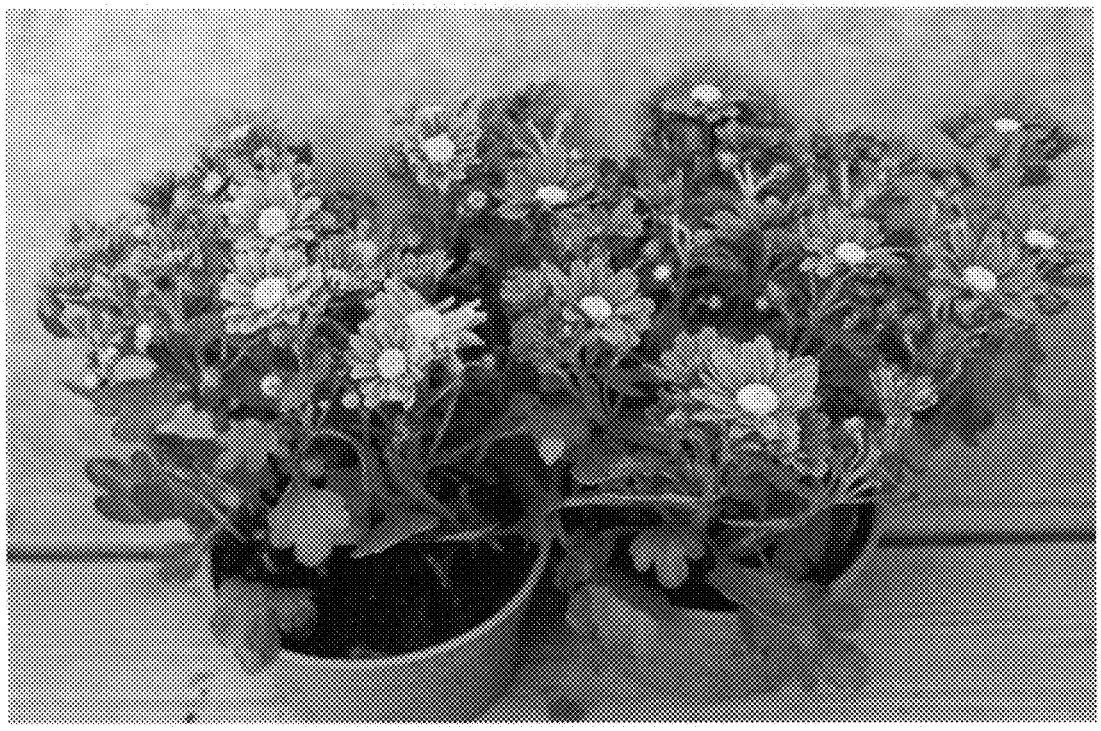

The photograph in FIG. 3 provides a comparison between 'Power Rosé' (left) and 'Power Purple' (right).

The Colors in the photograph may differ slightly from the color values cited in the detailed botanical description, which accurately describe the colors of the new *Chrysanthemum.*

DETAILED BOTANICAL DESCRIPTION

The following is a detailed description of plants of the new cultivar as grown in a 5-inch pan pot planted with 3 single pinched rooted cuttings and grown under greenhouse conditions at an average temperature of 65° F. for 10 weeks in Niagara on the Lake, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Commercial classification.*—Daisy-type spray pot *Chrysanthemum.*

*Flowering response.*—Early blooming, flowering occurs after short day treatment in about 52 days in spring, summer and fall and 56 days in winter.

*Plant type.*—Herbaceous, grown as a potted *Chrysanthemum* as a spray-type.

*Plant habit.*—Uniform, compact, mounded plant habit.

*Height and spread.*—Reaches about 15 cm in height and 24 cm in width when grown under the conditions tested under greenhouse conditions.

*Diseases resistance.*—No susceptibility or resistance to diseases common to *Chrysanthemum* has been observed under commercial greenhouse productions.

*Root description.*—Fibrous.

Growth and propagation:

*Propagation.*—Terminal stem cuttings.

*Time to root.*—About 8 days at 20° C.

*Production.*—Rooted cuttings grown at 65° F. finish in a 5-inch pan pot in 8 weeks.

*Growth rate.*—Vigorous.

Stem description:

*Stem color.*—138A with pubescence of 138B and 138C.

*Stem strength.*—Strong and flexible.

*Stem surface.*—Pubescent.

*Branching habit and quantity.*—Freely branched, about 5 branches per stem after removal of the apical meristem (pinching).

*Lateral branch size.*—About 10 cm in length and about 3.5 mm in width.

*Internode length.*—Lateral branches in a whorl from pinched node at base.

Foliage description:

*Leaf division.*—Simple.

*Leaf shape.*—Limb is broadly ovate and narrowing towards base.

*Leaf base.*—Limb base is cuneate, narrow base is truncate.

*Leaf apex.*—Rounded to broadly acute and minutely mucronate.

*Leaf margin.*—Matures to trifid to five-lobed with apex of lobes rounded with minute mucrunate tips.

*Leaf texture.*—Upper surface slightly pubescent, lower surface pubescent.

*Leaf venation.*—Palmate, color upper surface 144B near base and blending to leaf color towards apex, color lower surface 138B near base and blending to leaf color towards apex.

*Leaf attachment.*—Sessile.

*Leaf arrangement.*—Alternate.

*Leaf number.*—Average of 15 per lateral branch.

*Leaf internode length.*—Average of 1.2 cm.

*Leaf color.*—Young and mature foliage upper surface; between N137B and 138A, young and mature foliage lower surface; a blend of 138A and 138B.

*Leaf size* (*fully expanded*).—Average of 5 cm in length and 2.9 cm in width (expanded limb portion is an average of 3.6 cm in length).

*Fragrance of foliage.*—Fragrant if bruised.

Flower description:

*Inflorescence type.*—Composite, daisy form with oblong shaped ray florets and disk florets arranged acropetally on a capitulum, inflorescences typically borne in corymbs.

*Postproduction longevity.*—Conditions dependent, inflorescences maintain good color and substance for about 2 weeks in an interior environment.

*Fragrance.*—Faint.

*Quantity of inflorescences.*—Average of 10 per lateral stem, about 150 per plant produced from 3 cuttings.

*Inflorescence size.*—About 1 cm in depth and 3.8 cm in diameter, diameter of disk about 1.1 cm.

*Inflorescence buds.*—About 1 cm in depth and 8 mm in diameter, globose becoming ovate in shape prior to opening, N77B in color with phyllaries 138A to 138B.

*Peduncle.*—Strong, flexible, held from upright to an angle of 30° to vertical, surface is pubescent, an average of 2 cm in length and 2 mm in width, 138A in color with pubescence of 138B and 138C.

*Involucral bracts* (*phyllaries*).—Arranged in two layers, 138A to 138B in color with translucent margins, about 4.5 mm in length and 1.5 mm in width, surface is glandular and pubescence.

*Receptacle.*—About 4 mm in diameter and 3 mm in depth, 144A to 144C in color.

Ray florets (pistillate):

*Number.*—An average of 22.

*Arrangement.*—In 2 rows.

*Shape.*—Elongated oblong.

*Aspect.*—Emerge vertical and open to primarily horizontal when fully open.

*Size.*—An average of 1.6 cm in length and 6 mm in width.

*Ray floret apex.*—Rounded with one or two notches.

*Ray floret base.*—Cuneate.

*Ray floret margins.*—Entire.

*Ray floret texture.*—Glabrous on upper and lower surface and ridged.

*Ray floret color.*—Opening upper and lower surface; a blend of N77B and 71A and 71B (slightly lighter), fully open upper and lower surface; a blend of 70A, 70B and 70C, base surrounded pistil N144D.

Disk florets (perfect):

*Arrangement.*—Massed in center of receptacle.

*Quantity.*—Average of 97.

*Shape.*—Tubular.

*Size.*—About 5 mm in length and about 1.5 mm in width.

*Color.*—Immature 151B, mature 2A to 2C.

Reproductive organs:

*Presence.*—Disk florets are perfect, ray florets are pistillate.

*Gynoecium.*—1 Pistil per disk and ray floret, 4 mm in length, style color 154D, stigma color 12A.

*Androcoecium.*—5 stamens per disk floret, fused into tube surrounding style, anthers are translucent and color 154D, pollen is moderate in quantity and 14B in color.

*Seed.*—Seed production has not been observed under conditions tested.

It is claimed:

1. A new and distinct cultivar of *Chrysanthemum* plant named 'Power Rosé' as herein illustrated and described.

* * * * *